United States Patent [19]

Bauer et al.

[11] Patent Number: 5,248,641
[45] Date of Patent: Sep. 28, 1993

[54] PROCESS FOR PRODUCING BENTONITE CLAYS EXHIBITING ENHANCED SOLUTION VISCOSITY PROPERTIES

[75] Inventors: Patricia M. Bauer; David J. Hanlon; William R. Menking, all of Gonzales, Tex.

[73] Assignee: Southern Clay Products, Inc., Gonzales, Tex.

[21] Appl. No.: 849,807

[22] Filed: Mar. 11, 1992

Related U.S. Application Data

[63] Continuation of Ser. No. 583,288, Sep. 17, 1990, abandoned.

[51] Int. Cl.$^5$ .............................................. C04B 33/04
[52] U.S. Cl. .................................... 501/145; 501/146; 501/147; 106/416; 106/486
[58] Field of Search ............... 501/145, 146, 147, 127, 501/128; 106/416, 486, DIG. 4

[56] References Cited

U.S. PATENT DOCUMENTS

| | | | |
|---|---|---|---|
| 2,880,099 | 3/1959 | Andrieth | 501/147 |
| 3,106,476 | 10/1963 | Millman et al. | 501/147 |
| 3,115,416 | 12/1963 | Chavrier | 501/147 |
| 3,240,616 | 3/1966 | Harasowski et al. | |
| 3,574,345 | 4/1971 | Brociner | 259/148 |
| 3,700,474 | 10/1972 | Lang | |
| 3,779,782 | 12/1973 | Erickson et al. | |
| 4,242,140 | 12/1980 | Alther | |
| 4,279,547 | 7/1981 | Clem | |
| 4,371,626 | 2/1983 | Hentz | |

FOREIGN PATENT DOCUMENTS

| | | | |
|---|---|---|---|
| 2417303 | 11/1974 | Fed. Rep. of Germany | 501/147 |
| 0604866 | 4/1978 | U.S.S.R. | 501/147 |
| 815924 | 7/1959 | United Kingdom | |

OTHER PUBLICATIONS

G. R. Alther, "Improvement" Drilling Mud Properties of Low Grade Bentonites by Simultaneous Chemical Activation and Compaction, Interceram, vol. No. 5, pp. 501-503, 1982.

*Primary Examiner*—Karl Group
*Assistant Examiner*—Paul Marcantoni
*Attorney, Agent, or Firm*—Klauber & Jackson

[57] ABSTRACT

A process for upgrading a crude bentonite ore such that it can be used advantageously to prepare unusually high aqueous solution viscosities. This sequence comprises initially subjecting the crude ore to a working or shearing stage, followed by a drying step to about a 5% moisture level. $Na_2CO_3$ is then dry-blended with the material, and the sequence is completed by subjecting the mix to a pulverizing step.

15 Claims, No Drawings

PROCESS FOR PRODUCING BENTONITE CLAYS EXHIBITING ENHANCED SOLUTION VISCOSITY PROPERTIES

This application is a continuation of application Ser. No. 583,288, filed Sep. 17, 1990, now abandoned.

BACKGROUND OF THE INVENTION

This invention relates to a process for preparing bentonite clays, which when dispersed in water produce unexpectedly high solution viscosities. Such characteristics are highly desirable in numerous commercial applications.

Bentonites are naturally occurring ores which are mined in various regions of the world. Since these materials are highly colloidal and readily swell in water to form thixotropic gels, they are well-known for use as viscosity builders. This result obtains because bentonites are platey-type clays having a micaceous sheet structure. Such clays therefore are self-suspending, swelling and gelatinizing when mixed with water. Because of these viscosity building characteristics, bentonites find major utility as viscosity enhancers or builders in such areas as drilling muds and fluids, concrete and mortar additives, foundry and molding sands, compacting agents for gravel and sand as well as cosmetics.

Most natural bentonites are found in nature to exist in the sodium and/or the calcium form. The performance of a calcium bentonite as a viscosity builder can often be enhanced by its conversion to the sodium form.

The prior art details attempts to enhance the viscosity building characteristics of bentonite clays by several approaches. For the most part these involve working (or shearing) of the crude bentonite ore. The sequence generally calls for a (1) working, e.g. milling; (2) drying; and/or (3) pulverization sequence.

In some instances the use of an alkali pre-treatment is described to "activate" the clays, prior to the milling or working step.

Hentz, U.S. Pat. No. 4,371,626 thus discloses that alkali "activation" is only required for high calcium bentonite clays. It is suggested that there is an ion exchange mechanism involved where the sodium ion from either NaOH or $Na_2CO_3$ replaces the calcium ion. Hentz teaches that crude sodium bentonite can be upgraded with respect to its viscosity building characteristics, without alkali treatment, simply by (i) shearing the crude clay; (ii) drying the clay; and (iii) grinding/pulverizing the dried clay.

Alther, U.S. Pat. No. 4,242,140 describes a process for upgrading crude clays of the bentonite type by (i) adding 1-10% by weight of NaOH or $Na_2CO_3$ to the crude clay, or adding it during compacting step; (ii) compacting the activator treated material; and (iii) grinding.

No drying is required by the Alther process, the compacted clay requires no further drying, and is ground and screened to the desired mesh size.

Alther subsequently reviewed the state-of-the-art with respect to bentonite activation in a review article. He summarizes it as follows in "Improvement in Drill Mud Proper of Low Grade Bentonite by Simultaneous Chemical Activation and Compacting", INTERCERAM, Vol. NR 5, 1982, p. 503:

"State of the Art

Activation methods that are presently used are the following: 1. Sodium carbonate is spread in dry or dissolved form (dissolved in water) over the previously ripped bentonite bed and worked into the clay with a disc or roto-tiller. The bed is then frequently reworked over a period of several months to improve homogeneity. The sodium carbonate, if spread over the bed in dry form, will dissolve, due to the bentonite's inherent moisture, rain, water and snow. When activation is performed on the stockpile, a layer of 15 cm to 20 cm of bentonite is deposited. Sodium carbonate is then spread or sprinkled onto this layer, followed by discing. These steps are then repeated until the desired stockpile size is achieved. 2. Where bentonites are not field-dried, sodium carbonate may be added to wet crude bentonite en route to an extruder or multiple extruder stages, followed by drying. It is common to add water in addition to sodium carbonate to facilitate extrusion. The shearing action disorients the particles and increases the ion exchange. Here the bentonite is not dried and moisture is reduced to approximately 20% after extrusion. 3. The bentonite is first passed through a mechanical kneader, which works the sodium carbonate into the bentonite, and then steam is passed through the clay. The steam, whose low viscosity allows it to penetrate the clay aggregates, will split them and thus allow penetration and ion exchange. In addition the mobility of sodium ions is increased due to the action of the steam, increasing the exchange rate. 4. A pug mill may also be used, whereby the soda ash is sprinkled onto a field-dried bentonite during its stay on the conveyor belt, with subsequent pugging. Most of the above-listed methods have these parameters in common: they either require time, a large amount of energy, and lots of water, or all three parameters together. The author found that when a bentonite is compacted, while sodium carbonate is simultaneously being added, not only are time and energy saved, but the API properties (viscosity and water loss) appear to improve much more than with the use of traditional methods."

Lang, U.S. Pat. No. 3,700,474 teaches that the crude bentonite clays can be made more readily water dispersible by compacting the clay which has been previously pulverized. However, no mention is made in either the specification or claims with respect to the need for any drying sequence or addition of alkali or salt.

Goodman et al, U.S. Pat. No. 4,483,934 describes a method of beneficiating raw bentonite ore to improve its color. This involves the alkali treatment of the ore, working, shearing by milling followed by drying of the product.

It should be noted that in all the cases cited above, the prior art employs the use of an alkali or salt treatment as an "activator", either prior to or during the early milling or "working" stage of the sequence. In no instance is the addition of alkali considered or described as being added at the last step of the sequence, such as at "dry-blend", prior to pulverization, and as a matter of fact, such would be highly contrary to the prior art teachings.

SUMMARY OF THE INVENTION

It has now been unexpectedly found that by shifting the processing sequence from that described in the prior art, we can obtain a significantly enhanced sodium bentonite capable of unusually high solution viscosities.

The sequence that we have discovered unexpectedly represents a total reversal of the state-of-the art procedures and theories. This results in an unanticipated increase in the solution viscosity of a solution prepared with this inverted bentonite treatment.

The present invention calls for the initial working by shearing of a 20 to 50% water slurry of the crude ore, which has not had any salt treatment. The resultant product is then subsequently dried to about a 5 to 15% moisture level, preferably to about 5 to 10%, and more preferably to about 5 to 6% moisture. To this dried bentonite material is then added a "bentonite-activating" metal salt or hydroxide, typical of which is $Na_2CO_3$. The dry-blend is then pulverized. The preferred $Na_2CO_3$ salt is added in the general range of from 3 to 5%, although With certain crudes up to as much as 8% to 10% $Na_2CO_3$ can be useful.

Although both calcium bentonite and mixtures of calcium bentonite and sodium bentonite can benefit from the invention, it is preferred to use a predominantly calcium bentonite as the starting crude.

In accordance with the foregoing, it may be regarded as an object of the present invention, to provide a process modification which significantly improves (increases) the viscosity characteristics of aqueous bentonite solutions.

It is a further object of the invention to provide a method of upgrading bentonites, particularly calcium bentonites, without the need for any preliminary, lengthy aging/activation treatment.

DESCRIPTION OF THE PREFERRED EMBODIMENT

According to a preferred embodiment of this invention, the crude bentonite is initially subjected to shearing in a pug mill. Three or more passes through the milling process are often beneficial, but may not be required for many bentonites, wherein but a single pass confers most of the benefits of the invention. The pug mill can, for example, be of the type described in U.S. Pat. No. 3,574,345.

The sheared product thus obtained is then dried to a moisture level of about 5 to 6%; although higher levels o moisture can be used, up to 10 to 15%.

The dried product obtained at this stage of the sequence is then dry-blended or mixed with preferably about 3-5% $Na_2CO_3$ (in some instances up to about 8-10% $Na_2CO_3$ by weight can be beneficial), and the resultant mixture is then pulverized. This is distinguished from the prior art since the $Na_2CO_3$ salt in this case is added, by simple dry-blending, at the end of the process. The prior art teaches addition of salts such as $Na_2CO_3$, either to the ore stage or during the initial milling stage to activate the ore.

According to a further aspect of this invention, the following broad category of bentonite-activator salts and hydroxides will be effective in meeting the objectives of the invention:

Group IA periodic table cations including $Na^+$, $Li^+$, $K^+$ and $Cs^+$ in soluble salts and hydroxides, including carbonates and sulfates are considered useful. In Group IIA cations, $Mg^{++}$ in soluble salt form is useful. The transitional metals, $Ni^{++}$, $Zn^{++}$, $Cu^{++}$ and possibly $Co^{++}$ are considered useful. The above cations will be available as carbonate and sulfate salts or hydroxides. In specific instances, $(NH_4)_2CO_3$, $Al_2(SO_4)_3$ and $Fe_2(SO_4)_3$ may be useful activators for certain clays.

The preferred treatment of this invention involves the use of $Na_2CO_3$, which has been found to give the most beneficial results. The level of salt addition which has been found to be most effective is broadly between 1% and 10% based on the weight of bentonite; a preferred range is from 3 to 5% by weight, with the optimum level being about 5%.

Additionally, the embodiment of this invention may also include, but is not limited to, the use of an optional dispersing agent during the shearing step, such as tetrasodium pyrophosphate (TSPP) in amounts between about 1-5% by weight of the dry bentonite.

The invention is further illustrated by the following Examples, which are deemed to be illustrative, and not delimitive of the invention otherwise set forth.

EXAMPLE 1

A sample of a crude predominantly calcium bentonite clay wet cake containing 35% moisture and 2% tetrasodium pyrophosphate dispersant was sheared by being subject to one pass through a conventional pug mill, of the type aforementioned. The energy dissipated in the pass through the pug mill was about 30 Hp-hr/ton of dry solids. Upon completion of this working step, the material was dried in a Blue M ® oven until the moisture content was reduced to about 5%. The sample was then dry blended with 3% $Na_2CO_3$ and then pulverized. The sample was then added to water such that the solution represented 5% solids level. Brookfield viscosity data was measured at 30° C. using a No. 3 spindle, as 1100 cps.

EXAMPLE 2

The processing conditions of Example 1 were repeated, except that during the pugging step no TSPP was used. Instead, 2% TSPP, together with 3% sodium carbonate, were dry blended with the sample from the oven. The resulting Brookfield viscosity (No. 2 spindle) was 555 cps. (In all of Examples 1 to 7, the same crude was used.)

EXAMPLE 3

The conditions of Example 2 were repeated, except that no TSPP was used and 5% sodium carbonate was dry blended with the oven dried sample. The measured Brookfield viscosity (No. 3 spindle) was 1438 cps.

EXAMPLE 4

The procedure in this Example constituted a conventional processing and was a control. Specifically in this instance, a sample of the same crude bentonite clay, as in Example 1, was subjected to one pass through the pug mill in the presence therein of 5% sodium carbonate. The resulting product was dried as in Example 1 to the same moisture level, and the sample was then added to water and its Brookfield viscosity (spindle No. 1) evaluated as in Example 1 and found to be 32 cps.

EXAMPLE 5

In this Example, a further control was provided. No pugging was utilized. Instead, the sample at about 5 to 10% moisture was dry blended with 5% sodium carbonate and otherwise tested as in Example 1, and found to yield a viscosity (No. 3 spindle) of 920 cps.

EXAMPLE 6

This constituted a further control. The procedure used was identical to Example 4, except that three passes through the pug mill, each dissipating the mentioned approximate 30 Hp-hr/ton of dry solids, to a total of 90 Hp-hr/ton. The resulting product displayed a Brookfield viscosity (No. 1 spindle) of 16 cps.

EXAMPLE 7

The procedure was amenable to Example 3, except for the use of three passes through the pug mill. The measured viscosity (No. 3 spindle) was 1710 cps.

EXAMPLE 8

In this Example, (and in Example 9-11) a different bentonite crude was used than in prior Examples, but still constituting a predominantly calcium bentonite. The procedure used was the same as in Example 3, and was found to yield a viscosity (No. 1 of spindle) of 152 cps.

EXAMPLE 9

The procedure used was identical to that of control Example 4, except the crude was that of Example 8. The resulting viscosity (No. 1 spindle) was measured at 8 cps.

EXAMPLE 10

The procedure utilized in this Example was the same as in Example 8, except that 8% sodium carbonate was dry blended into the product from the oven. The resulting viscosity was measured (No. 3 spindle) at 600 cps.

EXAMPLE 11

The procedure utilized here was identical to that of Example 9, except that 8% sodium carbonate was used. The measured viscosity (No. 1 spindle) was 8 cps.

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

What is claimed is:

1. A process for enhancing the aqueous viscosity building characteristics of a bentonite clay; which comprises in sequence the steps of:
   (i) subjecting the crude bentonite ore to a shearing step as an aqueous workable 20 to 50% water slurry by subjecting said workable slurry to at least one pass through a pug mill;
   (ii) drying the product then obtained to a moisture content of 5-15%;
   (iii) adding between 1-10% of a bentonite-activating metal salt or hydroxide, based on solids as a dry-blend; and
   (iv) pulverizing the resultant blend into a powder.

2. The process of claim 1 wherein the bentonite-activating metal salt is selected from one or more members of the group comprising the water soluble carbonates and sulfates of Group IA and Group IIA periodic table cations.

3. The process of claim 1, wherein the product in step (ii) is dried to about 5 to 6% moisture.

4. The process of claim 1, wherein the salt employed is within the 3 to 5% range based on bentonite solids.

5. The process of claim 4, wherein the salt comprises sodium carbonate.

6. The process of claim 5, wherein the sodium carbonate level is 3-8%.

7. The process of claim 6, wherein the sodium carbonate level is about 5%.

8. The process of claim 1, wherein the bentonite activator is an alkali metal hydroxide.

9. The process of claim 8, wherein the hydroxide is sodium hydroxide.

10. The process of claim 1, wherein the bentonite crude ore is predominantly a calcium bentonite.

11. The process of claim 1, wherein the moisture content upon drying is about 5% in step (ii).

12. The process of claim 1, wherein a chemical dispersant is present in the wet slurry during the shearing step.

13. The process of claim 12, wherein the dispersant is tetrasodium pyrophosphate (TSPP).

14. The process of claim 12, wherein the TSPP is employed at a 1-5% level based on bentonite solids.

15. The process of claim 12, wherein about 3% of said sodium carbonate and about 2% of said dispersant are added.

* * * * *